(12) United States Patent
Aibara (10) Patent No.: US 11,653,858 B2
(45) Date of Patent: May 23, 2023

(54) RUNNING ANALYSIS DEVICE

(71) Applicant: CASIO COMPUTER CO., LTD., Tokyo (JP)

(72) Inventor: Takehiro Aibara, Hamura (JP)

(73) Assignee: Casio Computer Co., Ltd., Tokyo (JP)

( * ) Notice: Subject to any disclaimer, the term of this patent is extended or adjusted under 35 U.S.C. 154(b) by 484 days.

(21) Appl. No.: 16/827,617

(22) Filed: Mar. 23, 2020

(65) Prior Publication Data

US 2020/0305764 A1  Oct. 1, 2020

(30) Foreign Application Priority Data

Mar. 25, 2019 (JP) .............................. JP2019-055833

(51) Int. Cl.
*A61B 5/11* (2006.01)
*A61B 5/00* (2006.01)
*G01C 22/00* (2006.01)

(52) U.S. Cl.
CPC ............ *A61B 5/112* (2013.01); *A61B 5/6814* (2013.01); *A61B 5/6822* (2013.01);
(Continued)

(58) Field of Classification Search
CPC ............ A63B 24/0062; A63B 2220/40; A63B 2220/803; A63B 2220/836;
(Continued)

(56) References Cited

U.S. PATENT DOCUMENTS

| | | | | |
|---|---|---|---|---|
| 2007/0073514 A1* | 3/2007 | Nogimori | ............ | G01C 22/006 702/160 |
| 2016/0030804 A1* | 2/2016 | Mizuochi | ................. | A61B 5/11 482/8 |
| 2016/0367853 A1* | 12/2016 | Hirohama | .......... | G06K 9/00496 |

FOREIGN PATENT DOCUMENTS

| | | |
|---|---|---|
| JP | 2015-71000 A | 4/2015 |
| JP | 2016-32610 A | 3/2016 |
| JP | 2016-59729 A | 4/2016 |

OTHER PUBLICATIONS

Jarchi, Delaram, et al. "Gait parameter estimation from a miniaturized ear-worn sensor using singular spectrum analysis and longest common subsequence." IEEE Transactions on Biomedical Engineering 61.4 (2014): 1261-1273. (Year: 2014).*

(Continued)

*Primary Examiner* — Yoshihisa Ishizuka
*Assistant Examiner* — Carter W Ferrell
(74) *Attorney, Agent, or Firm* — Fitch, Even, Tabin & Flannery LLP (57) ABSTRACT

A running analysis device includes a processor and a memory storing a program. By executing the program, the processor performs obtainment, setting, and estimation processes. By the obtainment process, first data on an acceleration in an up direction perpendicular to a moving direction of a subject and second data on an acceleration in a direction opposite to the moving direction are obtained from a motion sensor attached to the subject's head or neck and including an acceleration sensor, the first and second data being detected by the acceleration sensor while the subject is running. By the setting process, a candidate time range including a candidate timing for a ground-contacting timing when a foot of the subject contacts the ground is set based on the first data. By the estimation process, the ground-contacting timing is estimated in the candidate time range, based on a timing when the second data is minimum.

12 Claims, 3 Drawing Sheets

(52) U.S. Cl.
CPC .......... *A61B 5/7203* (2013.01); *A61B 5/7278* (2013.01); *G01C 22/006* (2013.01); *A61B 2562/0219* (2013.01); *A63B 2225/50* (2013.01)

(58) Field of Classification Search
CPC ............ A63B 24/0006; A63B 69/0028; A63B 2225/50; A61B 5/112; A61B 5/6814; A61B 5/6822; A61B 5/7203; A61B 5/7278; A61B 2562/0219; A61B 2503/10; A61B 5/7235; A61B 5/6803; G01C 22/006
See application file for complete search history.

(56) References Cited

OTHER PUBLICATIONS

Hwang, Tong-Hun, et al. "Real-time gait analysis using a single head-worn inertial measurement unit." IEEE Transactions on Consumer Electronics 64.2 (2018): 240-248. (Year: 2018).*

* cited by examiner

RUNNING ANALYSIS DEVICE

CROSS-REFERENCE TO RELATED APPLICATIONS

This application is based upon and claims the benefit of priority from the prior Japanese Patent Application No. 2019-055833, filed on Mar. 25, 2019, the entire contents of which are incorporated herein by reference.

BACKGROUND

Technical Field

The present disclosure relates to a running analysis device.

Background Art

There is disclosed a conventional device that estimates, by utilizing an acceleration sensor attached to a user, ground-contacting timings when a foot of the user contacts the ground while the user is running (for example, disclosed in JP 2016-59729A).

However, the device disclosed in JP 2016-59729A is used by being attached to the waist of the user. The device attached to the head or the neck of the user cannot estimate the ground-contacting timings of the user while the user is running.

JP 2016-032610A discloses a technique for performing a process of detecting feature points (strike, mid-stance, lifting, etc.) of the running exercise performed by a user wearing an exercise analysis device on the trunk. Although JP 2016-032610A describes that "a preferred part is not limited to the trunk of the body, and the sensor (exercise analysis device) may be put on the head or a leg of a user, for example, rather than an arm" in paragraph [0257], it does not disclose any specific example of how to perform the process for detecting the above-mentioned feature points of the running exercise performed by the user wearing the device on the head.

SUMMARY

The present invention has been made in view of the above problems, and objects thereof include estimating ground-contacting timings of a user while the user is running by utilizing an acceleration sensor attached to the head or the neck of the user.

To achieve at least one of the abovementioned objects, according to an aspect of the present disclosure, there is provided a running analysis device including: a processor: and a memory that stores a program to be executed by the processor, wherein, by executing the program, the processor performs: an obtainment process by which first acceleration data on an acceleration in an up direction perpendicular to a moving direction of a subject and second acceleration data on an acceleration in a direction opposite to the moving direction of the subject are obtained from a motion sensor attached to a head or a neck of the subject and including an acceleration sensor, the first and second acceleration data being detected by the acceleration sensor while the subject is running; a setting process by which a candidate time range including a candidate timing for a ground-contacting timing when a foot of the subject contacts the ground is set based on the first acceleration data obtained by the obtainment process; and an estimation process by which the ground-contacting timing of the subject is estimated in the candidate time range set by the setting process, based on a timing when the second acceleration data obtained by the obtainment process has a minimum value.

BRIEF DESCRIPTION OF THE DRAWINGS

The accompanying drawings are not intended as a definition of the limits of the invention but illustrate embodiments of the invention, and together with the general description given above and the detailed description of the embodiments given below, serve to explain the principles of the invention, wherein.

DESCRIPTION OF EMBODIMENTS

The present invention is a running analysis device that can estimate ground-contacting timings of a user while the user is running by utilizing a motion sensor including an acceleration sensor and attached to the head or the neck of the user.

The "running" in the description below includes all kinds of movements of a person in which the person moves with his/her own leg(s), such as jogging, walking, and race walking.

Hereinafter, one or more embodiments of the present invention is described in detail with reference to the drawings. However, the present invention is not limited to the illustrated examples.

<Schematic Configuration of Running Analysis Device 100>

A running analysis device 100 in this embodiment is a device for estimating ground-contacting timings of a user (subject) when a foot of the user contacts the ground while the user is running. The running analysis device 100 is incorporated in: headphones, earphones, sunglasses or a running cap that are attached to the head of the user during running; a neck warmer or a necklace that are attached to the neck of the user during running; or the like.

Figure 1:
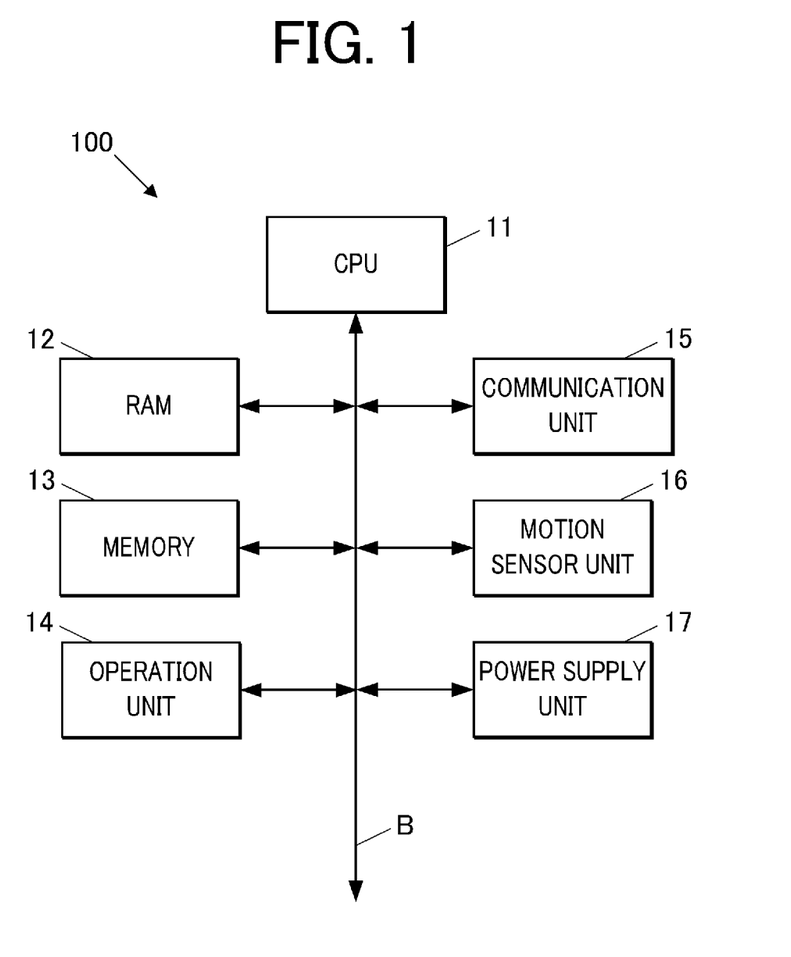
FIG. 1 is a block diagram showing a schematic configuration of a running analysis device 100 according to an embodiment to which the present invention is applied.

FIG. 1 is a block diagram showing a schematic configuration of the running analysis device 100 in this embodiment to which the present invention is applied.

As shown in FIG. 1, the running analysis device 100 includes a CPU (Central Processing Unit) 11, a RAM (Random Access Memory) 12, a memory 13, an operation unit 14, a communication unit 15, a motion sensor unit 16, and a power supply unit 17. Components of the running analysis device 100 are connected via a bus B.

The CPU 11 (obtainment unit, setting unit, estimation unit, smoothing unit, derivation unit, and determination unit) reads out various programs stored in the memory 13, such as a system program and application programs, loads the read programs into a work area of the RAM 12, and executes the loaded programs one by one in accordance with control signals input by the operation unit 14.

The RAM 12 is, for example, a volatile memory, and has the work area where the various programs and data read out by the CPU 11 are temporarily stored.

The memory 13 consists of a nonvolatile memory, for example, a flash memory. The memory 13 stores the various programs including a running analysis program that are executed by the CPU 11, data required to execute the programs, and so forth.

The operation unit 14 includes various buttons, such as a power button for turning on/off the running analysis device 100. In response to any of the various buttons being operated, the operation unit 14 outputs, to the CPU 11, an operation instruction corresponding to the operated button.

The communication unit 15 is an interface for exchanging data with external devices/apparatuses wirelessly. More specifically, the communication unit 15 includes an antenna, a modulation and demodulation circuit, and a signal processing circuit, and performs communication using a communication standard, such as Bluetooth®.

The motion sensor unit 16 includes: motion sensors, such as a three-axis acceleration sensor and a gyro sensor, capable of detecting motion of the running analysis device 100, namely motion of the head or neck of the user; an amplifier; and an AD converter. The motion sensor unit 16 amplifies analog sensing data detected by the motion sensors with the amplifier, converts the amplified analog sensing data into digital sensing data with the AD converter, and outputs the digital sensing data to the CPU 11.

The power supply unit 17 includes, for example, a battery. As the battery of the power supply unit 17, a secondary battery is used. The battery of the power supply unit 17 may be a primary battery, such as a button battery, instead of the secondary battery.

<Operation of Running Analysis Device 100>

Figure 2:
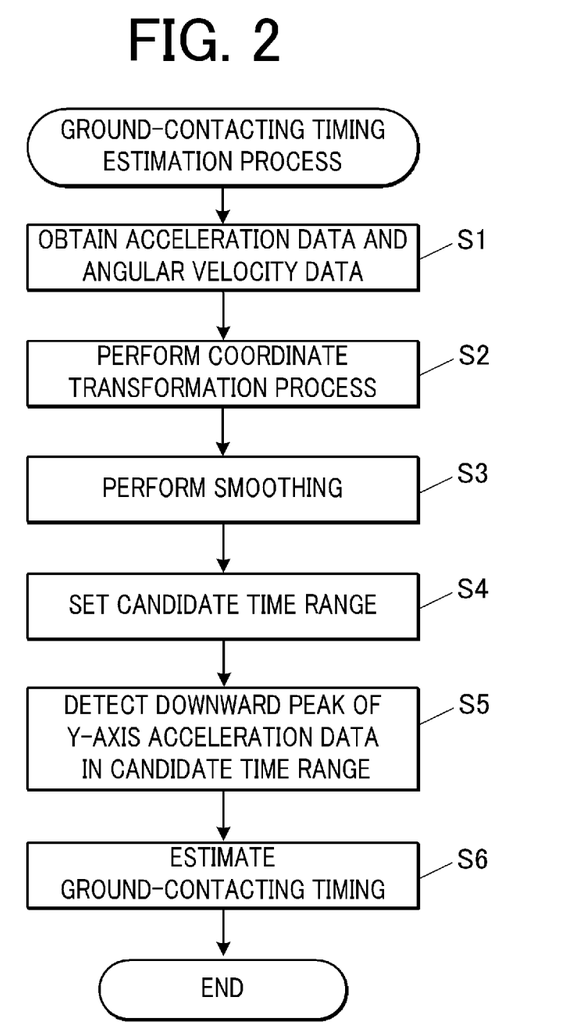
FIG. 2 is a flowchart showing a ground-contacting timing estimation process.
Figure 3:
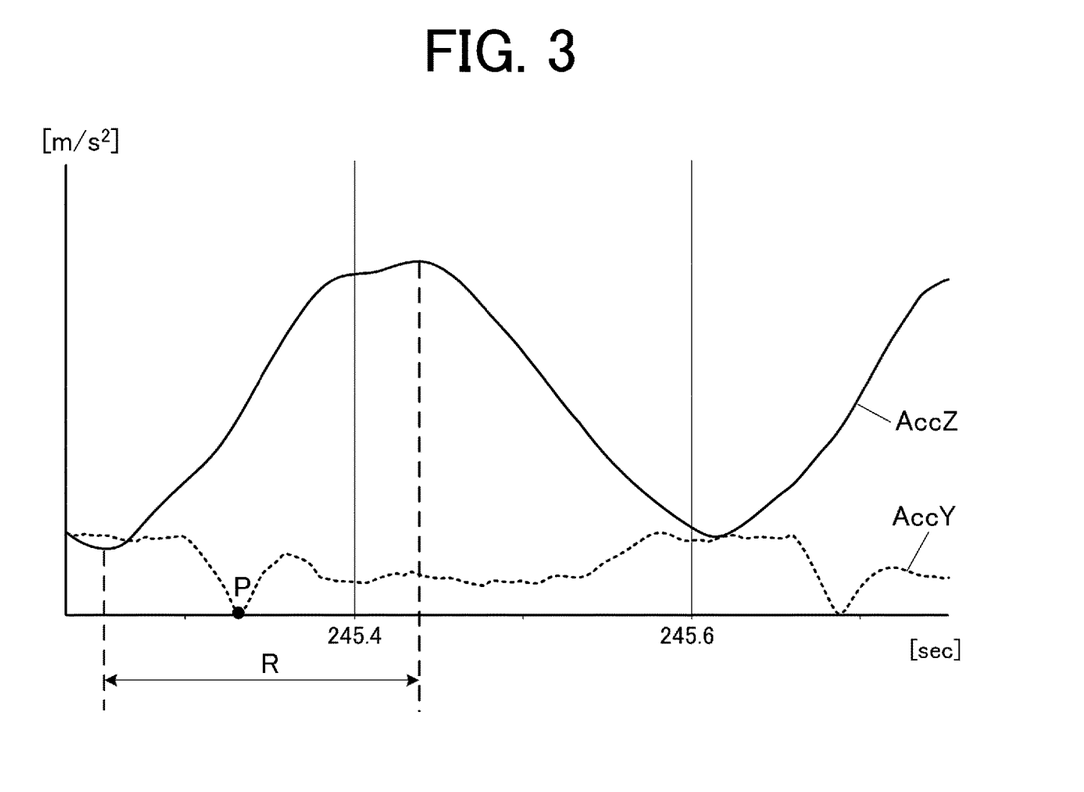
FIG. 3 is a graph illustrating part of Y-axis acceleration data and part of Z-axis acceleration data on which a smoothing process has been performed.

Next, the ground-contacting timing estimation process performed by the CPU 11 of the running analysis device 100 is described with reference to FIGS. 2 and 3. FIG. 2 is a flowchart showing the ground-contacting timing estimation process. FIG. 3 is a graph illustrating part of Y-axis acceleration data AccY and part of Z-axis acceleration data AccZ on which a smoothing process has been performed.

As shown in FIG. 2, the CPU 11 obtains acceleration data and angular velocity data detected by the three-axis acceleration sensor and the gyro sensor of the motion sensor unit 16, respectively (Step S1).

Next, the CPU 11 performs a coordinate transformation process by which the coordinate system of the acceleration data and the angular velocity data obtained from the motion sensor unit 16 is transformed from the sensor coordinate system into the world coordinate system (Step S2). In the world coordinate system, X-axis is the right-left direction of a user who is running, Y-axis is the front-back direction of the user, and Z-axis is the up-down direction of the user. In X-axis, the left direction is positive, and the right direction is negative. In Y-axis, the direction opposite to the moving direction of the user is positive, and the moving direction is negative. In Z-axis, the up direction is positive, and the down direction is negative.

Because the method of transforming the sensor coordinate system data into the world coordinate system data is well-known, the description thereof is omitted.

Next, the CPU 11 performs smoothing on the Y-axis acceleration data (second acceleration data) and the Z-axis acceleration data (first acceleration data) on which the coordinate transformation process has been performed (Step S3). More specifically, as the smoothing, the CPU 11 derives the moving average of each of the Y-axis acceleration data and the Z-axis acceleration data, wherein a mean is taken from 13 samples, for example.

Next, as shown in FIG. 3, the CPU 11 sets a time range from a timing when the Z-axis acceleration data AccZ on which the smoothing has been performed (hereinafter called AccZ data) has a minimum value (minimum point) to a timing when the AccZ data has a maximum value (maximum point) immediately after the minimum point as a candidate time range R that includes candidate timings for a ground-contacting timing (Step S4). The candidate time range R is from the minimum point to the maximum point appearing immediately after the minimum point of the AccZ data because, in a time range between a timing when the foot contacts the ground and a timing when the foot kicks the ground, acceleration in the up direction perpendicular to the moving direction of the user is equal to or greater than gravitational acceleration.

Next, as shown in FIG. 3, the CPU 11 detects the downward peak (minimum value) P of the AccY data in the candidate time range R (Step S5). The downward peak (minimum value) P of the AccY data is detected because, in response to the foot contacting the ground and being braked, the user's body tries to maintain a constant velocity in accordance with the law of inertia, and accordingly the head has acceleration in the moving direction.

Next, taking account of a time lag between an actual ground-contacting timing and a timing when acceleration at the actual ground-contacting timing is detected, the CPU 11 estimates the actual ground-contacting timing to be a timing a period of time prior to a timing when the downward peak (minimum value) P of the AccY data is detected, the period of time being, for example, a period during which three samples of the acceleration data are obtained by the acceleration sensor (Step S6), and ends the ground-contacting timing estimation process.

As described above, the running analysis device 100 analyses running of a user on the basis of sensing data obtained from motion sensors attached to the head or the neck of the user and including an acceleration sensor. More specifically, the running analysis device 100 obtains, as the sensing data, Z-axis acceleration data AccZ (first acceleration data) on acceleration in an up direction perpendicular to a moving direction of the user and Y-axis acceleration data AccY (second acceleration data) on acceleration in a direction opposite to the moving direction of the user, the first and second acceleration data being detected by the acceleration sensor while the user is running. On the basis of the obtained Z-axis acceleration data, the running analysis device 100 sets a candidate time range R including candidate timings for a ground-contacting timing when a foot of the user contacts the ground. The running analysis device 100 then estimates the ground-contacting timing of the user in the set candidate time range R on the basis of a timing when the Y-axis acceleration data has a minimum value.

That is, the running analysis device 100 can estimate the ground-contacting timing of the user who is running by utilizing the acceleration sensor attached to the head or the neck of the user.

Furthermore, the running analysis device 100 performs smoothing on the Z-axis acceleration data AccZ and the Y-axis acceleration data AccY. The running analysis device 100 then sets a candidate time range R on the basis of the Z-axis acceleration data AccZ on which the smoothing has been performed, and estimates the ground-contacting timing of the user in the candidate time range R on the basis of the timing when the Y-axis acceleration data AccY on which the smoothing has been performed has a minimum value (downward peak P). This can improve accuracy in estimating the ground-contacting timing.

Furthermore, the running analysis device 100 estimates the ground-contacting timing to be a timing a period of time prior to the timing when the Y-axis acceleration data AccY has the minimum value (downward peak P). Because the running analysis device 100 takes account of a time lag between the actual ground-contacting timing and a timing when acceleration at the ground-contacting timing is detected in order to estimate the ground-contacting timing, the accuracy in estimating the ground-contacting timing is further improved.

Furthermore, the running analysis device 100 is incorporated in an item to be attached to the head or the neck of the user, for example, head phones, earphones, sunglasses, a running cap, a neck warmer, a necklace, or the like. Thus, the user is simply required to wear an item that the user normally wears while running to cause the running analysis device 100 to estimate the ground-contacting timings of the user. This can reduce a burden on the user due to additional attachment of devices for estimating the ground-contacting timings. Further, the running analysis device 100 can estimate the ground-contacting timings of the user in natural running motions.

Although the above description discloses an example in which the flash memory as the memory 13 is used as a computer-readable storage medium storing the running analysis program of the present invention, the present invention is not limited to this. As other computer-readable media, a portable recording medium can be used. Further, as a medium to provide data of the running analysis program of the present invention via a communication line, a carrier wave can be used.

The above description is an example of the running analysis device, the running analysis method, and the running analysis program according to the present invention, and the present invention is not limited thereto.

For example, although the running analysis device 100 in the above embodiment includes the motion sensor unit 16 and the power supply unit 17, the motion sensor unit 16 and the power supply unit 17 may be configured in another body. That is, the running analysis device 100 may consist of two individual bodies: a main body for the running analysis device and a second body for the motion sensor unit and the power supply unit. It is possible that: the motion sensor unit in the second body detects acceleration and angular velocity of the user who is running, and stores data of the detected acceleration and angular velocity; and the running analysis device in the main body obtains, after the running, the data of the acceleration and angular velocity stored in the motion sensor unit and estimates ground-contacting timings of the user. In such a case, the second body for the motion sensor unit and the power supply unit is incorporated in an item to be attached to the head or the neck of the user. The main body for the running analysis device may be a terminal dedicated for performing running analysis, or a general-purpose PC or a portable terminal (for example, a smart phone, a smart watch, or the like).

Further, in the above embodiment, the CPU 11 of the running analysis device 100 takes account of a time lag between an actual ground-contacting timing and a timing when acceleration at the ground-contacting timing is detected, and estimates the actual ground-contacting timing to be a timing a period of time prior to a timing when the downward peak P (minimum value) of the AccY data is detected, the period of time being, for example, a time during which three samples of the acceleration are obtained by the acceleration sensor. That is, the CPU 11 uses a uniform period of time as a time lag to estimate actual ground-contacting timings. However, multiple periods of time corresponding to running speeds of users may be determined as time lags beforehand, and the CPU 11 (derivation unit, determination unit) may: derive a running speed of a user (subject) from, for example, a GPS sensor included in the motion sensors of the motion sensor unit 16; determine, as a time lag, a period of time corresponding to the derived running speed; and estimate an actual ground-contacting timing at the derived running speed to be a timing the determined period of time prior to the timing when the downward peak P (minimum value) of the AccY data is detected.

Further, in the above embodiment, the three-axis acceleration sensor and the gyro sensor are disclosed as examples of the motion sensors of the motion sensor unit 16. The running analysis device 100 may include a GPS sensor, a barometric sensor, a magnetic sensor, and/or a temperature sensor.

Naturally, the detailed configuration and the detailed operation of the running analysis device 100 in the above embodiment can be appropriately modified within the scope of the present invention.

Although some embodiments of the present invention have been described and illustrated in detail, the present invention is not limited to the embodiments described above but includes the scope of the present invention described in the scope of claims and the scope of their equivalents.

What is claimed is:

1. The claim is amended as follows:

A running analysis device comprising:

a processor: and a memory that stores a program to be executed by the processor, wherein, by executing the program, the processor performs:

an obtainment process by which first acceleration data on an acceleration in an up direction perpendicular to a moving direction of a subject and second acceleration data on an acceleration in a direction opposite to the moving direction of the subject are obtained from a motion sensor attached to a head or a neck of the subject and including an acceleration sensor, the first and second acceleration data being detected by the acceleration sensor while the subject is running;

a setting process by which a candidate time range including a candidate timing for a ground-contacting timing when a foot of the subject contacts ground is set based on the first acceleration data obtained by the obtainment process; and an estimation process by which the ground-contacting timing of the subject is estimated in the candidate time range set by the setting process, based on a timing when the second acceleration data obtained by the obtainment process has a minimum value, wherein:

by the estimation process, multiple periods of time corresponding to running speeds of the subject are determined for each running speed in advance, and the processor further performs:

a derivation process by which a running speed of the subject is derived, based on sensing data obtained from the motion sensor; and a determination process by which a period of time corresponding to the running speed derived by the derivation process is determined from among the multiple periods of time, and by the estimation process, the ground-contacting timing is estimated to be a timing of the determined period of time prior to the timing when the second acceleration data has the minimum value.

2. The running analysis device according to claim 1, wherein by the setting process, a time range between a timing when the first acceleration data has a minimum value and a timing when the first acceleration data has a maximum value immediately after the timing when the first acceleration data has the minimum value is set as the candidate time range.

3. The running analysis device according to claim 1, wherein
the processor further performs a smoothing process by which smoothing is performed on the first acceleration data and the second acceleration data obtained by the obtainment process,
by the setting process, the candidate time range is set based on the first acceleration data on which the smoothing is performed by the smoothing process, and
by the estimation process, the ground-contacting timing of the subject is estimated in the candidate time range, based on the timing when the second acceleration data on which the smoothing is performed by the smoothing process has the minimum value.

4. The running analysis device according to claim 1, wherein the running analysis device is incorporated in an item to be attached to the head or the neck of the subject.

5. The claim is amended as follows:
A running analysis method for a running analysis device, comprising:
obtaining that is obtaining first acceleration data on an acceleration in an up direction perpendicular to a moving direction of a subject and second acceleration data on an acceleration in a direction opposite to the moving direction of the subject from a motion sensor attached to a head or a neck of the subject and including an acceleration sensor, the first and second acceleration data being detected by the acceleration sensor while the subject is running;
setting that is setting a candidate time range including a candidate timing for a ground-contacting timing when a foot of the subject contacts ground, based on the first acceleration data obtained in the obtaining;
estimating that is estimating the ground-contacting timing of the subject in the candidate time range set in the setting, based on a timing when the second acceleration data obtained in the obtaining has a minimum value, wherein:
the estimating further includes,
determining multiple periods of time corresponding to running speeds of the subject for each running speed in advance, and
the method further comprises: deriving a running speed of the subject based on sensing data obtained from the motion sensor;
determining a period of time corresponding to the derived running speed from among the multiple periods of time; and
the estimating includes estimating the ground-contacting timing to be a timing of the determined period of time prior to the timing when the second acceleration data has the minimum value.

6. The running analysis method according to claim 5, wherein in the setting, a time range between a timing when the first acceleration data has a minimum value and a timing when the first acceleration data has a maximum value immediately after the timing when the first acceleration data has the minimum value is set as the candidate time range.

7. The running analysis method according to claim 5, further comprising smoothing that is performing smoothing on the first acceleration data and the second acceleration data obtained in the obtaining, wherein
in the setting, the candidate time range is set based on the first acceleration data on which the smoothing is performed, and
in the estimating, the ground-contacting timing of the subject is estimated in the candidate time range, based on the timing when the second acceleration data on which the smoothing is performed has the minimum value.

8. The running analysis method according to claim 5, wherein the running analysis device is incorporated in an item to be attached to the head or the neck of the subject.

9. The claim is amended as follows:
A non-transitory computer-readable storage medium storing a program that causes a computer of a running analysis device to function as:
an obtainment unit that obtains first acceleration data on an acceleration in an up direction perpendicular to a moving direction of a subject and second acceleration data on an acceleration in a direction opposite to the moving direction of the subject from a motion sensor attached to a head or a neck of the subject and including an acceleration sensor, the first and second acceleration data being detected by the acceleration sensor while the subject is running;
a setting unit that sets a candidate time range including a candidate timing for a ground-contacting timing when a foot of the subject contacts ground, based on the first acceleration data obtained by the obtainment unit; and
an estimation unit that estimates the ground-contacting timing of the subject in the candidate time range set by the setting unit, based on a timing when the second acceleration data obtained by the obtainment unit has a minimum value, wherein:
by the estimation unit,
multiple periods of time corresponding to running speeds of the subject are determined for each running speed in advance, and
the computer of the running analysis device further functions as:
a derivation unit by which a running speed of the subject is derived, based on sensing data obtained from the motion sensor; and
a determination unit by which a period of time corresponding to the running speed derived by the derivation unit is determined from among the multiple periods of time, and
by the estimation unit, the ground-contacting timing is estimated to be a timing of the determined period of time prior to the timing when the second acceleration data has the minimum value.

10. The storage medium according to claim 9, wherein the setting unit sets a time range between a timing when the first acceleration data has a minimum value and a timing when the first acceleration data has a maximum value immediately after the timing when the first acceleration data has the minimum value as the candidate time range.

11. The storage medium according to claim 9, wherein
the program further causes the computer to function as a smoothing unit that performs smoothing on the first acceleration data and the second acceleration data obtained by the obtainment unit, the setting unit sets the candidate time range, based on the first acceleration data on which the smoothing is performed by the smoothing unit, and the estimation unit estimates the ground-contacting timing of the subject in the candidate time range, based on the timing when the second acceleration data on which the smoothing is performed by the smoothing unit has the minimum value.

12. The storage medium according to claim 9, wherein the running analysis device is incorporated in an item attached to the head or the neck of the subject.

\* \* \* \* \*

UNITED STATES PATENT AND TRADEMARK OFFICE
CERTIFICATE OF CORRECTION

PATENT NO. : 11,653,858 B2  
APPLICATION NO. : 16/827617  
DATED : May 23, 2023  
INVENTOR(S) : Takehiro Aibara Page 1 of 1

It is certified that error appears in the above-identified patent and that said Letters Patent is hereby corrected as shown below:

In the Claims

In Column 6, Claim 1, Line 29, delete the sentence "The claim is amended as follows:"

In Column 7, Claim 5, Line 27, delete the sentence "The claim is amended as follows:"

In Column 8, Claim 9, Line 16, delete the sentence "The claim is amended as follows:"

In Column 8, Claim 10, Line 57, delete "The storage" and insert -- The non-transitory computer-readable storage --, therefor.

In Column 8, Claim 11, Line 63, delete "The storage" and insert -- The non-transitory computer-readable storage --, therefor.

In Column 9, Claim 12, Line 9, delete "The storage" and insert -- The non-transitory computer-readable storage --, therefor.

Signed and Sealed this  
Twenty-sixth Day of December, 2023

Katherine Kelly Vidal  
*Director of the United States Patent and Trademark Office*